(12) United States Patent
Paige et al.

(10) Patent No.: US 10,752,642 B1
(45) Date of Patent: Aug. 25, 2020

(54) MACROCYCLIC LACTONES

(71) Applicant: George Mason University, Fairfax, VA (US)

(72) Inventors: Mikell Paige, Fairfax, VA (US); Yun Michael Shim, Charlottesville, VA (US); Young-Ok You, Manassas, VA (US)

(73) Assignee: George Mason University, Fairfax, VA (US)

( * ) Notice: Subject to any disclaimer, the term of this patent is extended or adjusted under 35 U.S.C. 154(b) by 0 days.

(21) Appl. No.: 16/399,357

(22) Filed: Apr. 30, 2019

(51) Int. Cl.
*C07D 498/14* (2006.01)

(52) U.S. Cl.
CPC .................. *C07D 498/14* (2013.01)

(58) Field of Classification Search
CPC .................................................. C07D 498/14
See application file for complete search history.

(56) References Cited

U.S. PATENT DOCUMENTS

| | | | |
|---|---|---|---|
| 5,348,966 | A | 9/1994 | Starzl et al. |
| 8,591,946 | B2 | 11/2013 | Holm |
| 8,889,186 | B2 | 11/2014 | Holm et al. |
| 8,911,777 | B2 | 12/2014 | Coulter |
| 2010/0086592 | A1 | 4/2010 | Singh et al. |
| 2010/0297221 | A1 | 11/2010 | Coulter |
| 2011/0281906 | A1 | 11/2011 | Kondo et al. |
| 2011/0318277 | A1 | 12/2011 | Dalby et al. |
| 2016/0296500 | A1 | 10/2016 | Akoulitchev et al. |
| 2017/0072058 | A1 | 3/2017 | Sheng et al. |
| 2019/0015395 | A1 | 1/2019 | Appleford et al. |

OTHER PUBLICATIONS

Shivshankar. Journal of Drug Delivery Science and Technology, 2014, 24(5), 469-77 (Year: 2014).*
Perren. Neurobiology of Aging, 2014, 36, 1559-68 (Year: 2014).*
Balakin. Current Drug Discovery Technologies, 2005, 2, 99-113 (Year: 2005).*
Rutger, A. F.; Gjaltema, B.; Van Der Stoela. M.; Bersemaa, M. B.; and Bank, R. A. Disentangling mechanisms involved in collagen pyridinoline cross-linking: The immunophilin FKBP65 is critical for dimerization of lysyl hydroxylase 2. Proc. Natl. Acad. Sci. USA 2016, 113, 7142-7147.
Nagano, J.; Iyonaga, K.; Kawamura, K.; Yamashita, A; Ichiyasu, H.; Okamoto, T.; Suga, M. Sasaki, Y; and Kohrogi, H. Use of tacrolimus, a potent antifibrotic agent, in bleomycininduced lung fibrosis. Eur. Respir. J. 2006, 27, 460-9.
Clemons, P. A.; Gladstone, B. G.; Seth, A.; Chao, E. D.; Foley, M. A.; Schreiber, S. L Synthesis of Calcineurin-Resistant Derivates of FK506 and Selection of Compensatory Receptors. Chemistry & Biology, 2002, 9. 49-61.
Ertl, P.; Rohde, B.; and Selzer, P. Fast Calculation of Molecular Polar Surface Area as a Sum of Fragment-Based Contributions and Its Application to the Prediction of Drug Transport Properties. J. Med. Chem., 2000, 43, 3714-3717.

* cited by examiner

*Primary Examiner* — Noble E Jarrell
(74) *Attorney, Agent, or Firm* — Dave Law Group LLP; Raj S. Dave

(57) ABSTRACT

The present compositions and methods generally relate to the treatment of diseases, such as idiopathic pulmonary fibrosis (IPF) and neurodegenerative diseases related to tau aggregation. In particular, the compositions relate to compounds or pharmaceutically acceptable salts of Formula I:

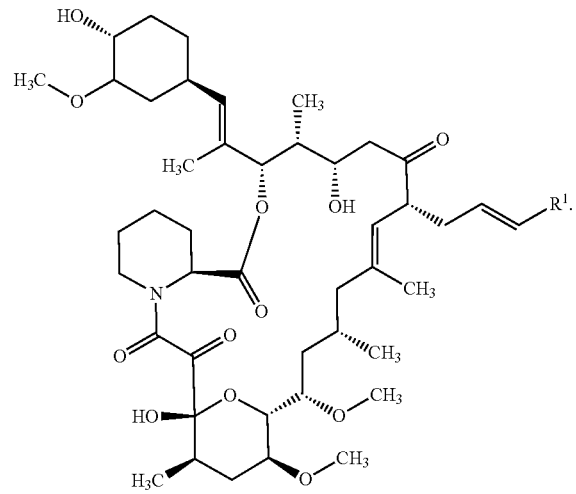

20 Claims, No Drawings

MACROCYCLIC LACTONES

CROSS-REFERENCE TO RELATED APPLICATION

None.

TECHNICAL FIELD

Embodiments described herein generally relate to compositions and methods for the treatment of diseases, such as idiopathic pulmonary fibrosis and neurodegenerative diseases related to tau aggregation. More particularly, the compositions and methods relate to 23-member macrocyclic lactones.

BACKGROUND

Idiopathic pulmonary fibrosis (IPF) is a fatal interstitial lung disease where the lungs become fibrotic and the patient struggles to breathe. IPF has a 5-year survival of rate of 30-50% and limited treatment options. It is believed that IPF develops from repeated alveolar injuries, leading to persistent signals for fibroblast activation, proliferation, and differentiation to myofibroblasts. The Food and Drug Administration has approved the drugs, pirfenidone (ESBRIET®) and nintedanib (OFEV® and GARGATEF®), for IPF treatment; however, despite the benefits these drugs can provide in improving quality of life, patients still experience precipitous drops in their respiratory function and high mortality rates.

FK506 or fujimycin (TACROLIMUS®) is a macrolide antibiotic that is currently being used for immunosuppression. It is believed to act principally through impairment of gene expression in target cells. For example, FK506 can bond to an immunophilin, FK506 binding protein. FK506 also has anti-fibrotic properties, but its immunosuppression properties can prevent it from being used as an anti-fibrotic. The challenge is to make an anti-fibrotic drug that does not cause immunosuppression.

Additionally, tau aggregation is a commonly observed event in many neurodegenerative disorders. Recent clinical and biochemical research has suggested that one of the protein chaperones, FKBP52, may play a role in certain types of tauopathy. However, limited chemical probes are available to study the function of this protein.

Therefore, there is a need for new compositions and methods that can be used to treat idiopathic pulmonary fibrosis and/or tauopathy.

SUMMARY

Disclosed herein are compositions that can include compounds or pharmaceutically acceptable salts of Formula I:

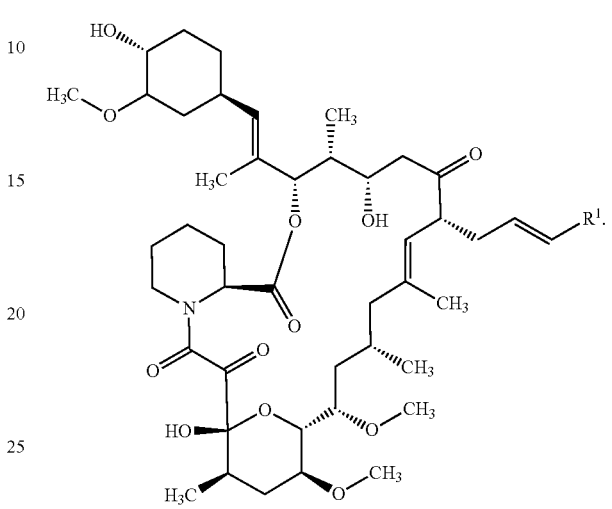

Formula I

Also disclosed are methods of using the compounds or pharmaceutically acceptable salts of Formula I in the treatment of diseases. In one specific embodiment, the compounds or pharmaceutically acceptable salts of Formula I can be used as an anti-fibrotic agent. In another specific embodiment, the compounds of Formula I can be used for the treatment of diseases associated with tau aggregation.

DETAILED DESCRIPTION

The compositions provided herein can include compounds of Formula I:

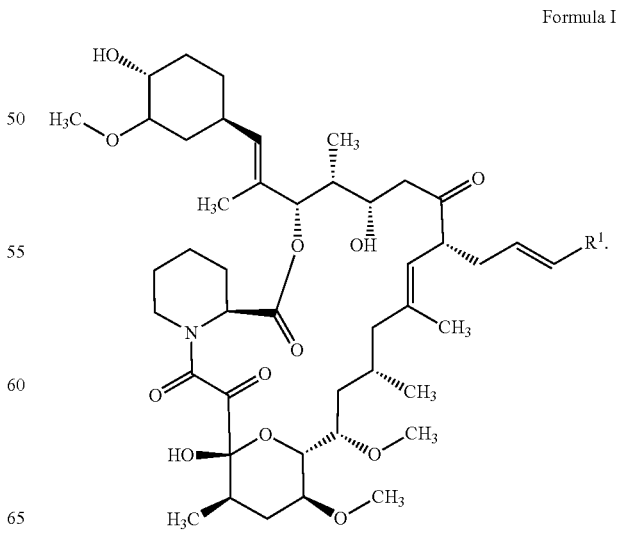

Formula I where R¹ can be independently selected from a group consisting of:

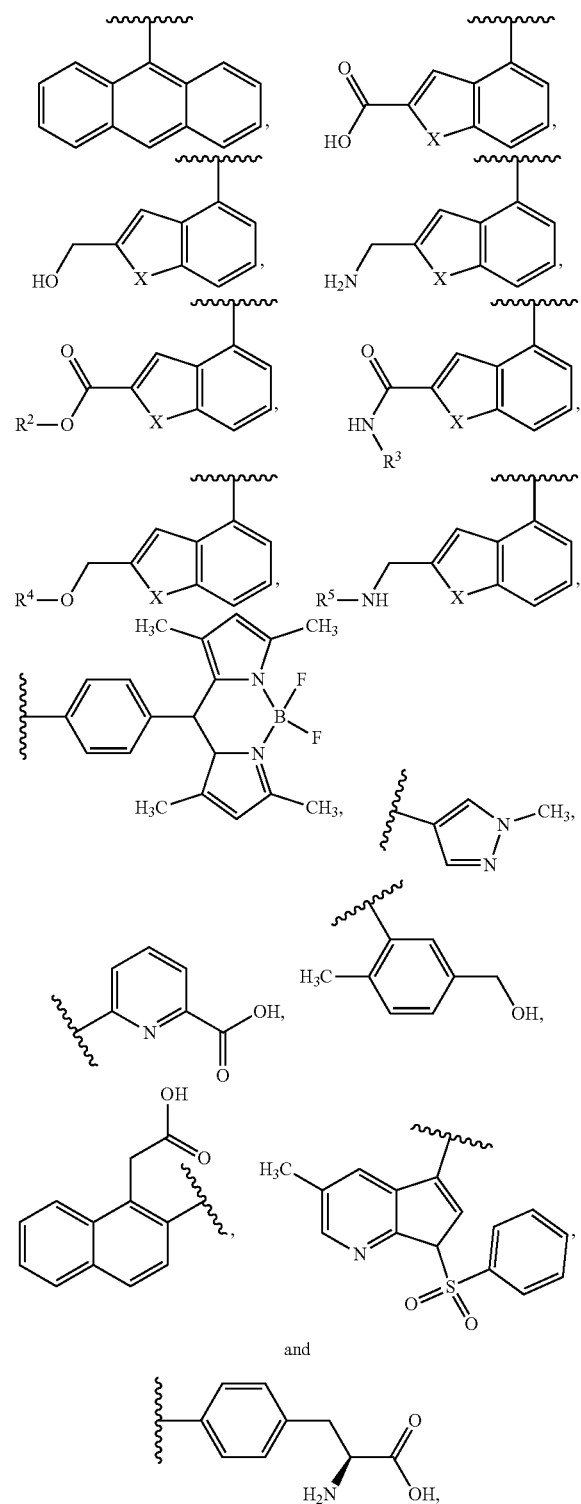

where R², R³, R⁴, and R⁵ can be independently selected from the group consisting of: H; F; Cl; Br; I; OH; ketone (═O); ether [—OR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; acyl halide (—COX); carbonyl [—COR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; aldehyde (—CHO); carbonate ester [—OCOOR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; carboxyl (—COOH); amide [—CONR'R", where R' and R" can be independently selected from hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; amines [—NR'R", where R' and R" can be independently selected from hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; cyanate (—OCN); isocynate (—NCO); nitrate (—ONO₂); nitrile (—CN); isonitrile (—NC); nitroso (—NO); oxime (—CH═NOH); borono —B(OH)₂; boronare [—B(OR')(R"), where R' and R" can be independently selected from hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; borinate [—B(R')(OR"), where R' and R" can be independently selected from hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; phosophino [—PR₂, where R can include hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; phosphono [—P(═O)(OH)(R), where R can include hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; phosphate (—OP(═O)(OH)₂; thiol (—SH); sulfide [—SR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; disulfide [—SSR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers], sulfinyl [—S(═O)R, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; sulfino (—SO$_2$H); sulfo (—SO$_3$H); thiocyanate; isothiocyanate; carbonothioyl [—C(=S)R where R can include methyl, ethyl, n-propyl, isopropyl, n-butyl, sec-butyl, isobutyl, tert-butyl; (C$_{2-4}$)alkenyl, such as ethenyl, propenyl, butenyl, where the double bond can be located at any position in the alkenyl carbon chain, and including any alkenyl conformational isomers]; (C$_{1-4}$)alkyl, such as methyl, ethyl, n-propyl, isopropyl, n-butyl, sec-butyl, isobutyl, tert-butyl; (C$_{2-4}$)alkenyl, such as ethenyl, propenyl, butenyl, where the double bond can be located at any position in the alkenyl carbon chain, and including any alkenyl conformational isomers; and where X can be independently selected from the group consisting of: CH, S, NH, and O.

It has been surprisingly and unexpectedly discovered that compounds of Formula I can have significant anti-fibrotic activity while causing little to no immunosuppression. The compounds of Formula I can inhibit and/or possibly reverse fibrosis in subjects afflicted with diseases that cause fibrosis, such as IPF. The compounds of Formula I can also be used in the treatment diseases associated with tau aggregation.

The compounds of Formula I can be provided in many forms. For example, the compounds of Formula I can include, but are not limited to, salts, hydrates, solvates, isomers, crystalline and non-crystalline forms, isomorphs, polymorphs, and metabolites thereof. The compounds of Formula I may exist in unsolvated and solvated forms. For example, when the solvent, such as water, is tightly bound, the complex will have a well-defined stoichiometry independent of humidity. When, however, the water is weakly bound, as in channel solvates and hygroscopic compounds, the water/solvent content can depend on humidity and drying conditions; hence, non-stoichiometry will be the norm. Moreover, the compounds of Formula I may exist in unsolvated as well as solvated forms with pharmaceutically acceptable solvents, such as water and ethanol. In general, the solvated forms are considered equivalent to the unsolvated forms. The compounds of Formula I may also exist in one or more crystalline states, i.e., polymorphs, or they may exist as amorphous solids.

Many of the compounds of Formula I may exist as geometric isomers or possess one or more asymmetric centers, thus existing as two or more stereoisomeric forms. The compounds of Formula I can include all the individual stereoisomers and geometric isomers of the compounds and mixtures thereof. Individual enantiomers can be obtained by chiral separation or using the relevant enantiomer in the synthesis.

The compounds of Formula I can include asymmetric carbons. When present in racemic compounds, solid and dotted wedges are used to define relative stereochemistry, rather than absolute stereochemistry. Racemic compounds possessing such indicated relative stereochemistry are marked with (+/−). Unless stated otherwise, it is intended that the compounds of Formula I can exist as stereoisomers, which include cis and trans isomers, optical isomers such as R and S enantiomers, diastereomers, geometric isomers, rotational isomers, conformational isomers, atropisomers, and mixtures thereof (such as racemates and diastereomeric pairs). The compounds of Formula I may exhibit more than one type of isomerism. Also included are acid addition or base addition salts wherein the counterion is optically active, for example, D-lactate or L-lysine, or racemic, for example, DL-tartrate or DL-arginine. When any racemate crystallizes, crystals of two different types are possible. The first type is the racemic compound (true racemate) where one homogeneous form of crystal is produced containing both enantiomers in equimolar amounts. The second type is the racemic mixture or conglomerate wherein two forms of crystal are produced in equimolar amounts each comprising a single enantiomer.

The compounds of Formula I can also include prodrugs. Thus, certain compounds of Formula I that may have little or no pharmacological activity themselves can, when administered into or onto the body, be converted into a compound having the desired activity, for example, by hydrolytic cleavage. Further information on the use of prodrugs may be found in "Pro-drugs as Novel Delivery Systems, Vol. 14, ACS Symposium Series (T. Higuchi and W. Stella) and "Bioreversible Carriers in Drug Design," Pergamon Press, 1987 (ed. E. B. Roche, American Pharmaceutical Association). Prodrugs can, for example, be produced by replacing appropriate functionalities present in the compounds of Formula I with certain moieties known to those skilled in the art as "pro-moieties" as described, for example, in "Design of Prodrugs" by H. Bundgaard (Elsevier, 1985).

The compounds of Formula I can include all pharmaceutically acceptable isotopically labeled compounds, which are identical to those recited herein, wherein one or more atoms are replaced by an atom having the same atomic number, but an atomic mass or mass number different from the atomic mass or mass number which predominates in nature. Examples of isotopes suitable for inclusion in the compounds of Formula I can include, but are not limited to, isotopes of hydrogen, such as $^2$H, $^3$H; carbon, such as $^{11}$C, $^{13}$C, and $^{14}$C; chlorine, such as $^{36}$Cl; fluorine, such as $^{18}$F; iodine, such as $^{123}$I and $^{125}$I; nitrogen, such as $^{13}$N and $^{15}$N; oxygen, such as $^{15}$O, $^{17}$O, and $^{18}$O; phosphorus, such as $^{32}$P; and sulfur, such as $^{35}$S. Certain isotopically-labeled compounds of Formula I, for example, those incorporating a radioactive isotope, are useful in drug and/or substrate tissue distribution studies (e.g., assays). The radioactive isotopes tritium, i.e., $^3$H, and carbon-14, i.e., $^{14}$C, are particularly useful for this purpose in view of their ease of incorporation and ready means of detection. Substitution with heavier isotopes such as deuterium, i.e., $^2$H, may afford certain therapeutic advantages resulting from greater metabolic stability, for example, increased in vivo half-life or reduced dosage requirements and, hence, may be preferred in some circumstances. Substitution with positron-emitting isotopes, such as $^{11}$C, $^{15}$F, $^{18}$F, $^{15}$O and $^{13}$N, can be useful in positron emission tomography studies for examining substrate receptor occupancy. Isotopically labeled compounds of Formula I can generally be prepared by conventional techniques or by processes analogous to those described in Scheme 1 or the Examples (see below) using an appropriate isotopically labeled reagent in place of the non-labeled reagent previously employed. Pharmaceutically acceptable solvates can include those wherein the solvent of crystallization may be isotopically substituted, e.g., D$_2$O, acetone-d$_6$, or DMSO-d$_6$. Compounds of Formula I can include, but are not limited to, isotopically labeled versions of these compounds, such as, but not limited to, the deuterated and tritiated isotopes and all other isotopes discussed above.

The compounds of Formula I can be provided in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

When a salt is intended to be administered to a subject the salt can be provided in a pharmaceutically acceptable form. A pharmaceutically salt can prepared by combining a compound of Formula I with an acid whose anion, or a base whose cation, is generally considered suitable for mammalian consumption. Pharmaceutically acceptable salts of the compounds of Formula I can have greater aqueous solubility relative to the parent compound.

Suitable pharmaceutically salts of the compounds of Formula I can include those derived from inorganic acids. The inorganic acids can include, but are not limited to, hydrochloric, hydrobromic, hydrofluoric, boric, fluoroboric, phosphoric, meta-phosphoric, nitric, carbonic, sulfonic, and sulfuric acids.

Suitable pharmaceutically salts of the compounds of Formula I can include those derived from organic acids. The organic acids can include, but are not limited to, aliphatic, cycloaliphatic, aromatic, araliphatic, heterocyclic, carboxylic, and sulfonic classes of organic acids. Specific examples of suitable organic acids can include, but are not limited to: acetate, trifluoroacetate, formate, propionate, succinate, glycolate, gluconate, digluconate, lactate, malate, tartrate, citrate, ascorbate, glucuronate, maleate, fumarate, pyruvate, aspartate, glutamate, benzoate, anthranilate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminoethansulfonate, algenic acid, p-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalene-sulfonate, oxalate, palmoate, pectinate, 3-phenylpropionate, picrate, pivalate, thiocyanate, and undecanoate.

Organic salts of the compounds of Formula I may be made from secondary, tertiary or quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups may be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), and arylalkyl halides (e.g., benzyl and phenethyl bromides).

Furthermore, when the compounds of Formula I carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

The compounds of Formula I or their pharmaceutically acceptable salts, I can be made using many synthetic strategies and known chemical transformations. The reaction Scheme 1, together with synthetic methods known in the art of organic chemistry, or modifications and derivatizations that are familiar to those of ordinary skill in the art, illustrate a method for preparing the compounds of Formula I. The starting materials used can be commercially available or may be prepared by routine methods known in the art. For example, the starting materials can be prepared by the methods discussed and described in the COMPENDIUM OF ORGANIC SYNTHETIC METHODS, Vol. I-XII (published by Wiley-Interscience).

The compounds of Formula I can be made using various Pd catalysts, such as in a Heck reaction. Scheme 1 depicts a Heck reaction that can be used to make compounds of Formula I.

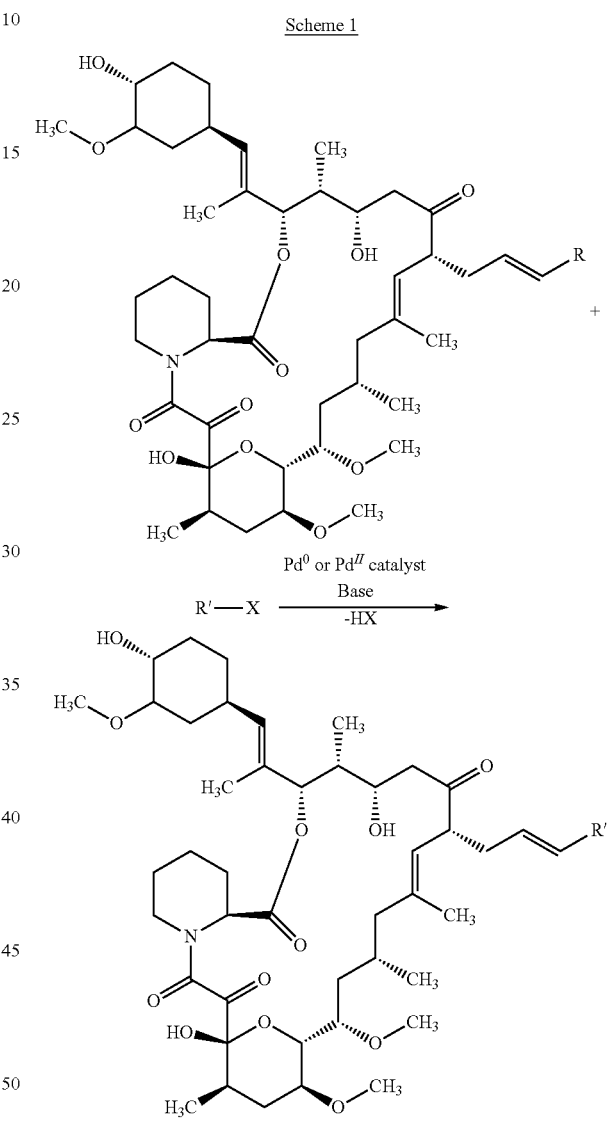

Furthermore, the $R^2$, $R^3$, $R^4$, and $R^5$ substituents and any derivatives of the compounds of Formula I can be made by known chemical transformations of the compounds' functional groups using standard chemical reactions. For example, these standard chemical reactions can include, but are not limited to: polar reactions under basic conditions, polar reactions under acidic conditions, pericyclic reactions, and free radical reactions. In another example, these standard chemical reactions can include, but are not limited to: addition reactions, substitution reactions, oxidation reactions, reduction reactions, elimination reactions, hydrolysis, acylation, amidations, etherification, and esterification. Alkane functional group transformations can include, but are not limited to: free radical chlorination (hv, $Cl_2$), free radical bromination (hv, $Br_2$), and allylic bromination (NBS). Alkene functional group transformations can include, but are not limited to: addition of HCl, addition of HBr, addition of HI, addition of $H_3O^+$, chlorination ($Cl_2$) bromination ($Br_2$), iodination ($I_2$), chlorohydrin formation ($Cl_2/H_2O$), bromohydrin formation ($Br_2/H_2O$), ether formation ($H^+/ROH$), oxymercuration ($Hg(OAc)_2/H_2O$), oxymercuration, ($Hg(OAc)_2/ROH$), hydroboration, epoxidation ($RCO_3H$), dihydroxylation ($OsO_4$), dihydroxylation ($KMnO_4$), cyclopropanation, dichlorocyclopropanation, ozonolysis (reductive workup), ozonolysis (oxidative workup), oxidative cleavage ($KMnO_4$), hydrogenation, rearrangements (H shift), rearrangements (alkyl shift), free radical addition of HBr, and Sharpless epoxidation. Alkyne functional group transformations can include, but are not limited to: deprotonation (acetylide formation), $S_N2$ with alkyl halides, partial reduction (Lindlar), partial, reduction ($Na/NH_3$), hydroboration, oxymercuration, addition of HCl, HBr, or HI, addition of HCl, HBr, or HI, hydrogenation, ozonolysis, oxidative cleavage ($KMnO_4$), and halogenation ($Cl_2$, $Br_2$, $I_2$). The substitution reaction can include, but is not limited to: alcohol formation, nitrile formation, thiol formation, ether formation, thioether formation, azides, ester formation, acetylide addition, alkanes (Gilman reagents), ammonium salt formation, alkyl chloride formation, alkyl bromide formation, alkyl iodide formation, alkyl shift, and hydride shift. Elimination reactions can include, but are not limited to: alkenes from alkyl halides, alkenes from alcohols (strong acid), alkenes from alcohols ($POCl_3$), alkenes from alkyl halides, E1 with rearrangement (alkyl shift), Hoffmann elimination, and alkyne formation via elimination E1 with rearrangement (hydride shift). Organometallic reactions can include, but are not limited to: Grignard formation (alkyl halides), Grignard formation (alkenyl halides), reaction of Grignards with acids, addition of Grignards to aldehydes, addition of Grignards to ketones, addition of Grignards to esters, reaction of Grignards with $CO_2$, addition of Grignards to nitriles, formation of organolithium reagents, formation of Gilman reagents, $S_N2$ with Gilman reagents, addition of Gilman reagents to enones, addition of Gilman to acyl halides, Heck reaction, Suzuki reaction, and Stille reaction. Reactions of epoxides can include, but are not limited to: epoxide opening (basic conditions), epoxide opening (acidic conditions), epoxide opening (diol formation), epoxide formation (from halohydrins), epoxide formation (from alkenes), and Sharpless epoxidation of alkenes. Reactions of alcohols and thiols can include, but are not limited to: deprotonation (alkoxide formation), protonation (onium ion formation), conversion to tosylates/mesylates, conversion to alkyl chlorides ($SOCl_2$), conversion to alkyl bromides ($PBr_3$), oxidation to aldehydes (PCC), oxidation to ketones (PCC+others), oxidation to carboxylic acid, ($H_2CrO_4$+ others), protection as silyl ethers, thiol formation ($S_N2$), and thiol oxidation to disulfides. Reactions of dienes can include, but are not limited to: Diels-alder reaction, polymerization of dienes, reactions of aromatics (arenes), nitration ($HNO_3/H_2SO_4$), chlorination ($Cl_2$ plus catalyst), bromination ($Br_2$ plus catalyst), sulfonylation ($SO_3/H_2SO_4$), Friedel Crafts alkylation (R—X plus catalyst), Friedel Crafts acylation (RCOX plus catalyst), iodination ($I_2$/catalyst), side chain oxidation ($KMnO_4$), reduction of nitro groups, reduction of aromatic ketones, side chain bromination, nucleophilic aromatic substitution ($S_NAr$), and aryne formation ($S_NAr$ via arynes). Reactions of aldehydes and ketones can include, but are not limited to: hydrate formation ($H_2O$), cyanohydrin formation (CN), reduction of aldehydes ($NaBH_4$), reduction of aldehydes ($LiAlH_4$), reduction of ketones ($NaBH_4$), reduction of ketones ($LiAlH_4$), Grignard addition to aldehydes, Grignard addition to ketones, acetal formation ($ROH/H^+$), acetal hydrolysis ($H_3O^+$), imine, formation ($RNH_2$), enamine formation ($R_2NH$), Wolff-Kishner: reduction to alkanes, Clemmensen, reduction to alkanes, oxidation to carboxylic acid ($H_2CrO_4$ or $KMnO_4$), keto-enol tautomerism, enolate formation, aldol addition reaction, alkylation of enolates, Wittig reaction (alkene formation), thioacetal formation, imine hydrolysis, oxidation to carboxylic acids (Tollens), haloform reaction, Baeyer-Villiger reaction, aldol condensation, Cannizarro reaction. Reactions of carboxylic acids can include, but are not limited to: deprotonation (carboxylate formation), formation via Grignard and $CO_2$, conversion to acid chloride ($SOCl_2$), reduction ($LiAlH_4$), Fischer esterification, and decarboxylation (of β-keto acids). Reactions of esters can include, but are not limited to: reduction to aldehydes (DIBAL-H), reduction to alcohols ($LiAlH_4$), hydrolysis to carboxylic acid (acidic), hydrolysis to carboxylic acid (basic), addition of Grignard reagents to esters, Claisen condensation, and transesterification (basic conditions). Reactions of acyl halides can include, but are not limited to: conversion to esters (ROH), conversion to carboxylic acids ($H_2O$), conversion to anhydrides ($RCO_2$), conversion to amides ($RNH_2$), conversion to ketones (Gilman reagents), and conversion to aldehydes ($LiAlH(OtBu)_3$). Reactions of α,β-unsaturated ketones (enones) can include, but are not limited to: Michael reaction (conjugate addition of enolates), conjugate addition of Gilman reagents, conjugate addition of other nucleophiles. Reactions of amines and amides can include, but are not limited to: dehydration of amides to nitriles ($P_2O_5$), Hofmann rearrangement, Gabriel synthesis of amines, reductive amination, formation of diazonium salts, reactions of diazonium salts, amide formation using DCC, amide formation from acid halides, and Curtius rearrangement. Reactions of nitriles can include, but are not limited to: addition of Grignard reagents to nitriles, reduction to amines ($LiAlH_4$), and hydrolysis to carboxylic acids. Chemical reactions and reagents that may be utilized to make derivatives and prodrugs of the compounds of Formula I are described in M. B. Smith, *March's Advanced Organic Chemistry*, 7$^{th}$ edition, 2013.

One skilled in the art will recognize that in some cases, the compounds of Formula I made by various synthetic strategies and chemical transformations will be generated as a mixture of diastereomers and/or enantiomers; these may be separated at various stages of the synthetic scheme using conventional techniques or a combination of such techniques, such as, but not limited to, crystallization, normal-phase chromatography, reversed phase chromatography and chiral chromatography, to afford the single enantiomers of the compounds of Formula I.

During any of the following synthetic sequences, it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991; and T. W. Greene and P. G. M. Wuts, Protective Groups in Organic Chemistry, John Wiley & Sons, 1999; and T. W. Greene and P. G. M. Wuts, Protective Groups in Organic Chemistry, John Wiley & Sons, 2006, which are hereby incorporated by reference.

The diseases that can be treated with compounds of Formula I can include, but are not limited to: idiopathic pulmonary fibrosis, amyotropic lateral sclerosis, Alzheimer's disease, Parkinson's disease, Huntington's disease, and other syncleinopathies and taupathies, such as Parkinson's disease dementia and frontotemporal lobe dementia and other dementia's and memory loss conditions which may be associated with age related increases with neurotoxic protein aggregation and/or increased oxidative stress or to defect of autophagy (the cells mechanism for removing damaged cellular components). The compounds of Formula I can also be used to relieve oxidative stress and promote autophagy.

Suitable subjects that can be treated by compounds of Formula I can include mammalian subjects. Mammals can include, but are not limited to, canine, feline, bovine, caprine, equine, ovine, porcine, rodents, lagomorphs, and primates. In one embodiment, the subjects are humans. Human subjects may be of either gender and at any stage of development.

The compounds of Formula I can be incorporated into pharmaceutical compositions. For example, a pharmaceutical composition can include a mixture of one or more compounds of Formula I and one or more pharmaceutically acceptable carriers. In another example, a pharmaceutical composition can include a mixture of one or more compounds of Formula I, one or more pharmaceutically acceptable carriers, and one or more adjuvants. Other pharmacologically active substances can also be present. The compounds of Formula I can be administered as a compound per se or the compounds of Formula I can be administered as pharmaceutically acceptable salts. Pharmaceutically acceptable salts of compounds of Formula I can have greater aqueous solubility relative to the parent compound.

Compositions that include compounds of Formula I can be formulated according to known methods for preparing pharmaceutically useful compositions. Formulations are described in detail in a number of sources which are well known and readily available to those skilled in the art. For example, *Remington's Pharmaceutical Science* by E. W. Martin describes how to make pharmaceutical formulations. In general, the compositions that include compounds of Formula I can be formulated such that an effective amount of at least one compound of Formula I is combined with a suitable pharmaceutically acceptable carrier or diluent in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically acceptable carriers and diluents which are known to those skilled in the art.

The pharmaceutically acceptable carriers or diluents for use with compounds of Formula I can include, but are not limited to: water, saline, oils including mineral oil, ethanol, dimethyl sulfoxide, gelatin, cyclodextrans, magnesium stearate, dextrose, cellulose, sugars, calcium carbonate, glycerol, alumina, starch, and equivalent carriers and diluents, or mixtures of any of these.

The adjuvants can include, but are not limited to, wetting agents, stabilizing agents, binding agents, dispersing agents, emulsifying agents, suspending agents, bioadhesive agents, polymers, and flavoring agents. The preservative can include, but is not limited to benzalkonium chloride. The polymer can include, but is not limited to, polyacrylic acid, polyvinyl alcohol, hyaluronic acid, hydroxypropylmethyl cellulose, hydroxyethyl cellulose, methyl cellulose, and heteropolysaccharide polymers, such as gelan gum.

To provide for the administration of such dosages for the desired therapeutic treatment, pharmaceutical compositions of the compounds of Formula I can be from a low of about 0.05% and to a high of about 99.9% by weight of the total of one or more of the compounds or pharmaceutically acceptable salts of Formula I based on the weight of the total composition, including a pharmaceutically acceptable carrier and any adjuvant. For example, the pharmaceutical compositions of compounds or pharmaceutically acceptable salts of Formula I can have compounds or pharmaceutically acceptable salts of Formula I from about 0.05 wt % to about 99.9 wt %, 0.05 wt % to about 10 wt %, 0.2 wt % to about 5 wt %, 1 wt % to about 20 wt %, 5 wt % to about 45 wt %, 8 wt % to about 65 wt %, or 15 wt % to about 85 wt %, based on the weight of the total composition, including any pharmaceutically acceptable carrier and/or adjuvant.

The pharmaceutically acceptable carriers can be a solid, a liquid, or both, and may be formulated with the compound as a unit-dose composition, for example, a tablet, which can contain from a low of about 0.05 wt % to a high of about 99.9 wt % of the active compounds. The pharmaceutical compositions of compounds of Formula I can be coupled with suitable polymers as targetable pharmaceutically acceptable carriers.

Other pharmaceutically acceptable carriers and modes of administration known in the pharmaceutical art may also be used. Pharmaceutical compositions of compounds of Formula I may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman et al., Eds., Pharmaceutical Dosage Forms, Marcel Decker, New York, N.Y., 1980; and Kibbe et al., Eds., Handbook of Pharmaceutical Excipients ($3^{rd}$ Ed.), American Pharmaceutical Association, Washington, 1999.

The compounds of Formula I can be used alone or in combination with other therapeutic and/or active compounds in the treatment of various conditions or disease states. The compounds of Formula I and other compounds may be administered simultaneously (either in the same dosage form or in separate dosage forms) or sequentially. The administration of two or more compounds "in combination" means that the two compounds are administered closely enough in time that the presence of one alters the biological effects of the other. The two or more compounds may be administered simultaneously, concurrently or sequentially. Additionally, simultaneous administration may be carried out by mixing the compounds prior to administration or by administering the compounds at the same point in time but at different anatomic sites or using different routes of administration. The phrases "concurrent administration," "co-administration," "simultaneous administration," and "administered simultaneously" mean that the compounds are administered in combination.

The compounds of Formula I may be administered by any suitable route, preferably in a form of a pharmaceutical composition adapted to such a route, and in a dose effective for the treatment intended. The active compounds and compositions, for example, may be administered orally, rectally, parenterally, or topically (e.g., intranasal or ophthalmic).

The compounds of Formula I and compositions thereof can be administered to a subject orally, topically, and/or by injection. Oral administration may involve swallowing, so that the compound enters the gastrointestinal tract, or buccal or sublingual administration may be employed, by which the compound enters the blood stream directly from the mouth.

The compounds of Formula I may be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

The compounds of Formula I can be formulated such that administration topically to the skin or mucosa (i.e., dermally or transdermally) leads to systemic absorption of the compounds. The compounds of Formula I can also be formulated such that administration intranasally or by inhalation leads to systemic absorption of the compound.

The dosage regimen for the compounds of Formula I can be based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions. The total daily dose of a compounds of Formula I (administered in single or divided doses) is typically from about 0.01 mg/kg to about 100 mg/kg. In another embodiment, the total daily dose of the compound of Formula I is from about 0.1 mg/kg to about 50 mg/kg, and in another embodiment, from about 0.5 mg/kg to about 30 mg/kg (i.e., mg compound of Formula I per kg body weight). In one embodiment, dosing is from about 0.01 mg/kg/day to about 10 mg/kg/day. In another embodiment, dosing is from about 0.1 mg/kg/day to about 1.0 mg/kg/day. Dosage unit compositions may contain such amounts or submultiples thereof to make up the daily dose. In many instances, the administration of the compound will be repeated a plurality of times in a day (typically no greater than 4 times). Multiple doses per day may be used to increase the total daily dose, if desired. Intravenously, doses may range from about 0.1 to about 10 mg/kg/minute during a constant rate infusion.

Oral administration of a solid dose form can be presented in discrete units, such as hard or soft capsules, pills, cachets, lozenges, or tablets, each containing a predetermined amount of at least one compound of Formula I. In another embodiment, the oral administration may be in a powder or granule form. In another embodiment, the oral dose form is sub-lingual, such as, for example, a lozenge. In such solid dosage forms, the compounds of Formula I are ordinarily combined with one or more adjuvants. Such capsules or tablets may contain a controlled-release formulation. In the case of capsules, tablets, and pills, the dosage forms also may comprise buffering agents or may be prepared with enteric coatings.

For oral administration, the compounds of Formula I can be provided in the form of tablets containing from about 0.01 mg to about 0.05 mg, about 0.1 mg to about 0.5 mg, about 1.0 mg to about 2.5 mg, about 5.0 mg to about 10.0 mg, about 15.0 mg to about 25.0 mg, about 50.0 mg to about 75.0 mg, about 100 mg to about 125 mg, 150 mg to about 175 mg, about 200 mg to about 250 mg, and 0.01 mg to about 500 mg of the active ingredient for the symptomatic adjustment of the dosage to the patient. In another example, the compounds of Formula I can be provided in the form of tablets containing from about 0.05 wt % to about 99.9 wt %, 0.05 wt % to about 10 wt %, 0.2 wt % to about 5 wt %, 1 wt % to about 20 wt %, 5 wt % to about 45 wt %, 8 wt % to about 65 wt %, or 15 wt % to about 85 wt % of compounds of Formula I, based on the weight of the total composition, including any pharmaceutically acceptable carrier and/or adjuvant.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). For example, the compounds of Formula I can be provided in a liquid form containing from about 0.05 wt % to about 99.9 wt %, 0.05 wt % to about 10 wt %, 0.2 wt % to about 5 wt %, 1 wt % to about 20 wt %, 5 wt % to about 45 wt %, 8 wt % to about 65 wt %, or 15 wt % to about 85 wt % of compounds of Formula I, based on the weight of the total composition, including any pharmaceutically acceptable carrier and/or adjuvant.

In another embodiment, the pharmaceutical compositions of the compounds of Formula I can include a parenteral dose form. Parenteral administration can include, but is not limited to, subcutaneous injections, intravenous injections, intraperitoneal injections, intramuscular injections, intrasternal injections, and infusion. Injectable preparations (i.e., sterile injectable aqueous or oleaginous suspensions) may be formulated according to the known art using suitable dispersing, wetting, and/or suspending agents, and include depot formulations.

The compounds of Formula I can be administered a topical dose form. Topical administration can include, but is not limited to, transdermal administration, such as via transdermal patches or iontophoresis devices, intraocular administration, or intranasal or inhalation administration. Compositions for topical administration can include, but is not limited to, topical gels, sprays, ointments, and creams. A topical formulation can include a compound that enhances absorption or penetration of the active ingredient through the skin or other affected areas. When the compounds of Formula I are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibers, bandages and microemulsions. Liposomes can also be used. Typical carriers include alcohol, water, mineral oil, liquid petrolatum, white petrolatum, glycerin, polyethylene glycol and propylene glycol. Penetration enhancers may be incorporated-see, for example, Finnin and Morgan, J. Pharm. Sci., 88 (10), 955-958 (1999).

For intranasal administration or administration by inhalation, the active compounds of Formula I are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone; as a mixture, for example, in a dry blend with lactose; or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may include a bioadhesive agent, for example, chitosan or cyclodextrin.

The compounds of Formula I can be used in kits that are suitable for use in performing the methods of treatment described above. In one embodiment, the kit contains a first dosage form comprising one or more of the compounds of the present invention and a container for the dosage, in quantities sufficient to carry out the methods of the present invention.

The compounds of Formula I can also be administered utilizing liposome technology, slow release capsules, implantable pumps, and biodegradable containers. These delivery methods can, advantageously, provide a uniform dosage over an extended period of time.

Various techniques may be used to increase bioavailability of the compounds of Formula I. For example, prodrugs of compounds of Formula I can be prepared. Prodrugs employ various physical and chemical modifications to improve features of the active drug, and in some embodiments may be viewed as pharmacologically inactive prodrug functional groups that undergo a chemical transformation or enzymatic cleavage to liberate the active parent drug and produce the desired effect in the body. Utilizing a prodrug approach can yield benefits such as enhanced solubility, improved selective targeting of drugs to anatomical sites, protection from rapid metabolism and elimination, reduction toxic effects of an active drug on other parts of the body, and enhanced patient compliance.

Non-limiting examples of techniques useful for enhancing the bioavailability of compounds or pharmaceutically acceptable salts of Formula I can include the use of co-solvents, hydrotropy, micronization, change in dielectric constant of solvent, amorphous forms, chemical modification of the drug, use of surfactants, inclusion complex, alteration of pH of solvent, use of hydrates or solvates, use of soluble prodrugs, application of ultrasonic waves, functional polymer technology, controlled precipitation technology, evaporative precipitation in aqueous solution, use of precipitation inhibitors, solvent deposition, precipitation, selective adsorption on insoluble carriers, size reduction technologies, lipid based delivery systems, micellar technologies, porous micro particle technology, solid dispersion technique, and various types of solid dispersion systems.

Other methods for enhancement of bioavailability, such as by the enhancement of solubility, are described in Reddy M. S. et al., "Solubility enhancement of fenofibrate, a BCS class II drug, by self-emulsifying drug delivery systems," *International Research Journal of Pharmacy*, 2011, 2(11): 173-177; Khamkar G S, "Self micro emulsifying drug delivery system (SMEED) o/w microemulsion for BCS Class II drugs: an approach to enhance oral bioavailability," *International Journal of Pharmacy and Pharmaceutical Sciences*, 2011, 3(3):1-3; Elgart A et al., "Improved oral bioavailability of BCS class 2 compounds by self nano-emulsifying drug delivery systems (SNEDDS): the underlying mechanisms for amiodarone and talinolol", Pharm Res., 2013 December; 30(12):3029-44; Singh N. et al., "Techniques for bioavailability enhancement of BCS class II drugs: a review," *International Journal of Pharmaceutical and Chemical Science*, 2013, 2(2):1092-1101; Elkihel L. et al., "Synthesis and orally macrofilaricidal evaluation of niclosamide lymphotropic prodrugs," *Arzneimittelforschung*, 1994, 44(11): 1259-64; and Kansara H. et al., "Techniques used to enhance bioavailability of BCS class II drugs: a review," *Int. J. Drug Dev. & Res.*, 2015, 7(1):82-93.

The method of using compounds or pharmaceutically acceptable salts of Formula I can include, but is not limited to, packaged dosage formulations and kits. A packaged dosage formulation can including one or more containers of one or more compounds of Formula I formulated in a pharmaceutically acceptable dosage. The package can contain discrete quantities of the dosage formulation, such as tablet, capsules, lozenge, and powders. The quantity of compound in a dosage formulation and that can be administered to a patient can vary from about 1 mg to about 5000 mg, about 1 mg to about 2000 mg, about 1 mg to about 500 mg, about 5 mg to about 250 mg, or about 10 mg to about 100 mg.

The kits can be packaged into suitable packaging material, optionally in combination with instructions for using the kit components, e.g., instructions for using compounds of Formula I. In one embodiment, a kit includes an amount of at least one compound of Formula I, and instructions for administering at least one compound of Formula I to a subject in need of treatment on a label or packaging insert. In further embodiments, a kit includes an article of manufacture, for delivering at least one compound of Formula I into a subject locally, regionally or systemically.

As used herein, the term "packaging material" refers to a physical structure housing the components of the kit. The packaging material can maintain the components in a sterile state, and can be made of material commonly used for such purposes (e.g., paper, corrugated fiber, glass, plastic, foil, ampules, etc.). The label or packaging insert can include appropriate printed and/or digital instructions, for example, for practicing a method of the invention. Thus, in additional embodiments, a kit includes a label or packaging insert including instructions for practicing a method of the invention in solution, in vitro, in vivo, or ex vivo.

Instructions can therefore include instructions for practicing any of the methods of using compounds of Formula I described herein. For example, pharmaceutical compositions can be included in a container, pack, or dispenser together with instructions for administration to a subject to treat a disease. Instructions may additionally include indications of a satisfactory clinical endpoint or any adverse symptoms that may occur, storage information, expiration date, or any information required by regulatory agencies such as the Food and Drug Administration or European Medicines Agency for use in a human subject.

The instructions may be digital or on "printed matter," e.g., on paper or cardboard within the kit, on a label affixed to the kit or packaging material, or attached to a vial or tube containing a component of the kit. Instructions may comprise voice or video tape and additionally be included on a computer readable medium, such as a disk (diskette or hard disk), optical CD such as CD- or DVD-ROM/RAM, magnetic tape, electrical storage media such as RAM and ROM and hybrids of these such as magnetic/optical storage media.

Each component of the kit can be enclosed within an individual container or in a mixture, and all of the various containers can be within single or multiple packages. Kits can include packaging material that is compartmentalized to receive one or more containers such as vials, tubes, and the like, each of the container(s) including one of the separate elements to be used in a method described herein. Packaging materials for use in packaging pharmaceutical products include, by way of example only U.S. Pat. Nos. 5,323,907, 5,052,558 and 5,033,252. Examples of pharmaceutical packaging materials can include, but are not limited to, blister packs, bottles, tubes, pumps, bags, vials, light-tight sealed containers, syringes, bottles, and any packaging material suitable for a selected formulation and intended mode of administration and treatment.

A kit may include one or more additional containers, each with one or more of various materials desirable from a commercial and user standpoint for use of the compounds for treating or preventing diseases. Non-limiting examples of such materials include, but not limited to, buffers, diluents, carrier, package, container, vial and/or tube labels listing contents and/or instructions for use, and package inserts with instructions for use.

A label can be on or associated with a container containing a compounds of Formula I. A label can be on a container when letters, numbers or other characters forming the label are attached, molded or etched into the container itself, a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In some embodiments of the kit, the compounds of the Formula I can be presented in a pack or dispenser device which can contain one or more unit dosage forms containing a compound disclosed herein. The pack can for example contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a compound provided herein formulated in a compatible pharmaceutically acceptable carrier can also be prepared, placed in an appropriate container, and labeled for treatment of an indicated condition.

Examples

In order to provide a better understanding of the foregoing discussion, the following non-limiting examples are offered. Although the examples can be directed to specific embodiments, they are not to be viewed as limiting the invention in any specific respect.

The synthesis of compound 1 (anthracene moiety) is shown in the following reaction scheme:

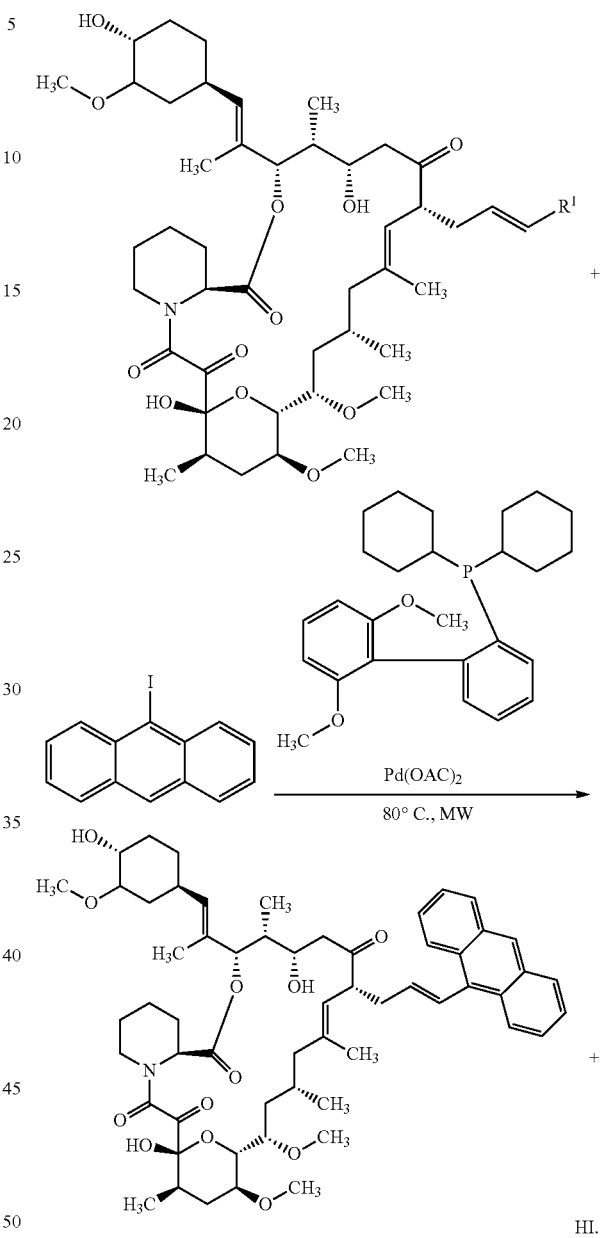

Compound 1 was made by adding FK-506 hydrate (200 mg, 0.243 mmol, 822 g/mol), iodoanthracene (148 mg, 0.486 mmol, 304.13 g/mol), Pd(OAc)$_2$ (27.3 mg, 0.122 mmol, 224.5 g/mol), and SPhos (50 mg, 0.122 mmol, 410.53 g/mol) to a microwave reaction vial. The microwave reaction vial was capped and purged with nitrogen. Acetonitrile (4 mL, degassed with nitrogen) and trimethylamine (0.1 mL, 0.0.729 mmol, 101.19 g/mol) were added to the microwave reaction vial to make a reaction mixture. The reaction mixture was heated to 60° C. for 4 hours in a microwave reactor. Then, acetonitrile (4 mL, degassed with nitrogen) was added to the reaction mixture, and the reaction mixture was heated to 80° C. for 12 more hours. At the completion of the reaction time, the solvent was removed from the reaction mixture under reduced pressure. The crude product was collected and purified using 20 vol % acetonitrile in dichloromethane on a high performance silica gel column. Compound 1 (194 mg) was obtained as a mixture of isomers at the olefin moiety, and validated by MALDI-TOF. The $R_f$ by TLC was 0.22 and 0.36 for the mixture of isomers eluting with a 1:3 acetonitrile-dichloromethane mobile phase on a normal phase silica gel plate.

The hydrophobicity of a compound can affect its absorption, bioavailability, hydrophobic drug-receptor interactions, metabolism of molecules, and toxicity. Table 1 gives the calculated solubility partition coefficients for various compounds of the Formula I.

TABLE 1

| Calculated Properties | | | |
|---|---|---|---|
| Compound | R | miLogP | TPSA |
| 1 | (9-anthracenyl group) | 4.30 | 0 |
| 2 | (BODIPY-phenyl group) | -2.25 | 8.82 |
| 3 | (1-methylpyrazol-4-yl group) | 0.39 | 17.83 |
| 4 | (6-carboxypyridin-2-yl group) | 0.34 | 50.19 |
| 5 | (3-methyl-4-hydroxymethylphenyl group) | 1.72 | 20.23 |
| 6 | (naphthalen-1-yl acetic acid group) | 2.55 | 37.30 |

TABLE 1-continued

| Calculated Properties | | | |
|---|---|---|---|
| Compound | R | miLogP | TPSA |
| 7 | (methylcyclopenta-pyridinyl phenylsulfonyl group) | 2.67 | 51.97 |
| 8 | (4-(2-amino-2-carboxyethyl)phenyl group) | -1.23 | 63.32 |

The miLogP and the topological polar surface area (TPSA) were calculated using the CHEMOFFICE® suite of programs. The miLogP is based on molecular fragments contributions, which can characterize the intramolecular H-bonding contribution and charge interactions. TPSA, uses functional group contributions based on a large database of structures to calculate polar surface area that avoids the need to calculate ligand 3D structures or to decide which is the relevant biological conformation or conformations. Further discussion of calculating a compound's hydrophobicity can be found in Ertl P., Rohde B., and Selzer P., *J Med Chem.* 2000 Oct. 5; 43(20):3714-7.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility. It is therefore intended by the appended claims to cover any and all such applications, modifications and embodiments within the scope of the present invention.

Certain embodiments and features have been described using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated. It should also be appreciated that the numerical limits may be the values from the examples. Certain lower limits, upper limits and ranges appear in at least one claims below. All numerical values are "about" or "approximately" the indicated value, and take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application.

What is claimed is:

1. A compound or a hydrate, solvate, geometric isomer, or salt thereof, wherein the compound has a chemical structure:

Formula I

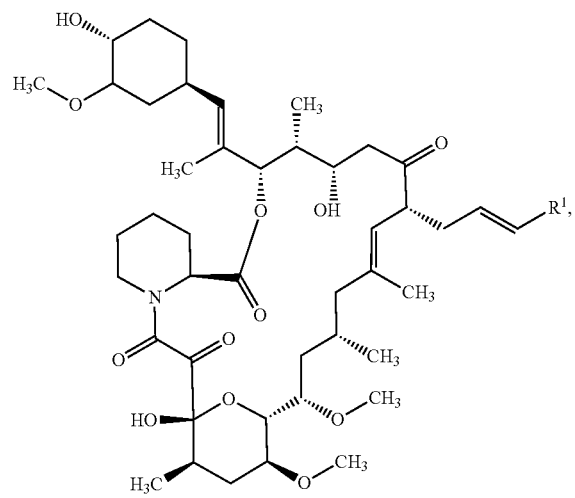

wherein $R^1$ is independently selected from a group consisting of:

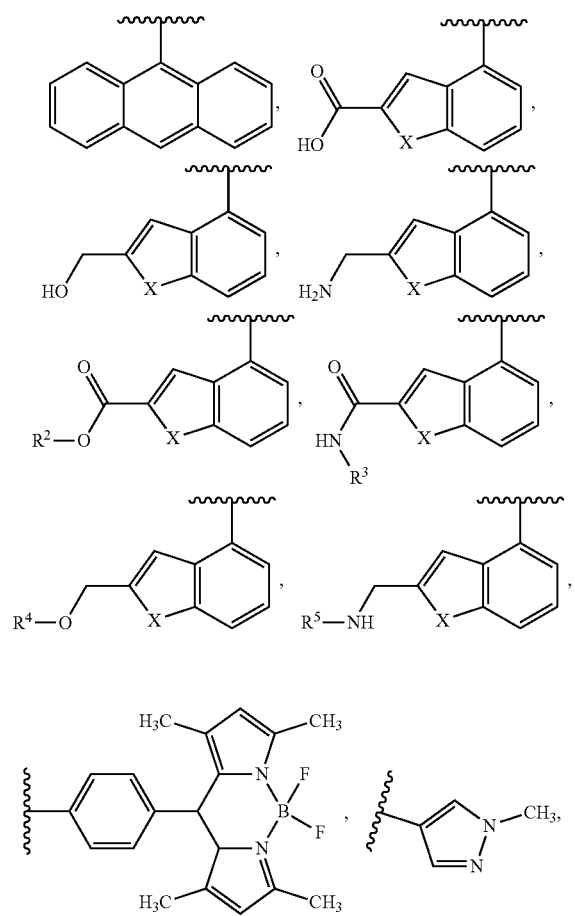

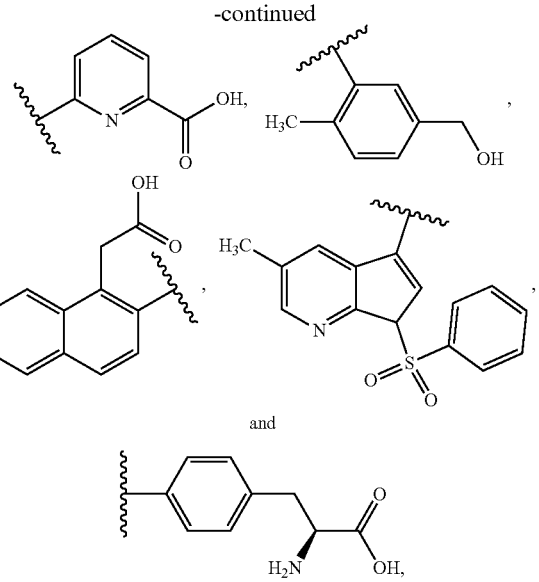

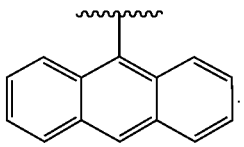 [SMILES: *c1c2ccccc2cc2ccccc12]

and

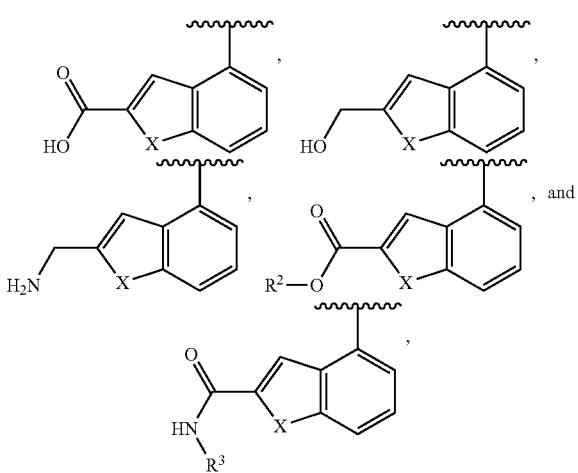

wherein $R^2$, $R^3$, $R^4$, and $R^5$ are independently selected from a group consisting of: H, ketone, ether, acyl halide, carbonyl, aldehyde, carbonate ester, carboxyl, amide, amines, cyanate, isocynate, nitrate, nitrile, isonitrile, nitroso, oxime, borono, borinate, phosophino, phosphono, phosphate, thiol, sulfide, disulfide, sulfinyl, sulfino, sulfo, thiocyanate, isothiocyanate, carbonothioyl, $(C_{1-4})$alkyl, and $(C_{2-4})$alkenyl, and wherein X is independently selected from a group consisting of $CH_2$, S, NH, and O.

2. The compound of claim 1, wherein $R^1$ is:

3. The compound of claim 1, wherein $R^1$ is selected from a group consisting of:

wherein R² and R³ are independently selected from a group consisting of: H, ketone, ether, acyl halide, carbonyl, aldehyde, carbonate ester, carboxyl, amide, amines, cyanate, isocynate, nitrate, nitrile, isonitrile, nitroso, oxime, borono, borinate, phosophino, phosphono, phosphate, thiol, sulfide, disulfide, sulfinyl, sulfino, sulfo, thiocyanate, isothiocyanate, carbonothioyl, (C₁₋₄)alkyl, and (C₂₋₄)alkenyl, and wherein X is independently selected from a group consisting of: CH₂, S, NH, and O.

4. The compound of claim 1, wherein R¹ is selected from a group consisting of:

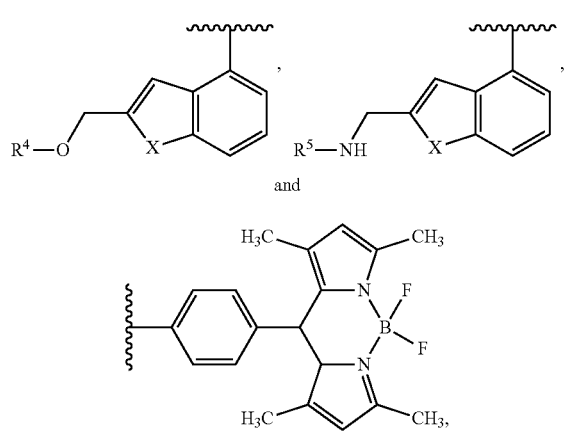

wherein R⁴ and R⁵ are independently selected from a group consisting of: H, ketone, ether, acyl halide, carbonyl, aldehyde, carbonate ester, carboxyl, amide, amines, cyanate, isocynate, nitrate, nitrile, isonitrile, nitroso, oxime, borono, borinate, phosophino, phosphono, phosphate, thiol, sulfide, disulfide, sulfinyl, sulfino, sulfo, thiocyanate, isothiocyanate, carbonothioyl, (C₁₋₄)alkyl, and (C₂₋₄)alkenyl, and wherein X is independently selected from a group consisting of: CH₂, S, NH, and O.

5. The compound of claim 1, wherein R¹ is selected from a group consisting of:

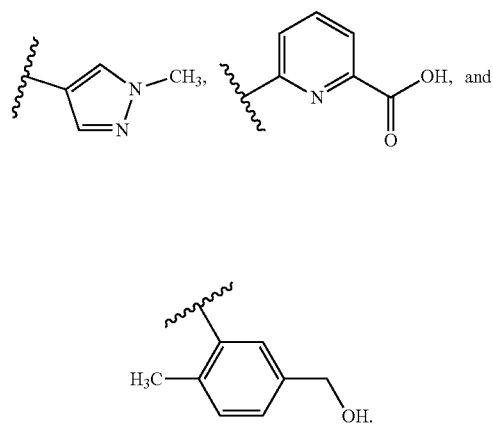

6. The compound of claim 1, wherein R¹ is selected from a list consisting of:

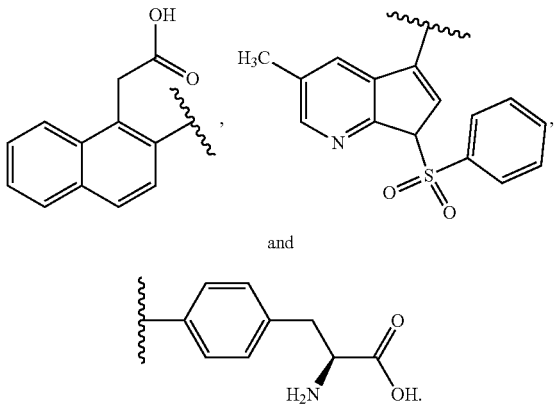

and

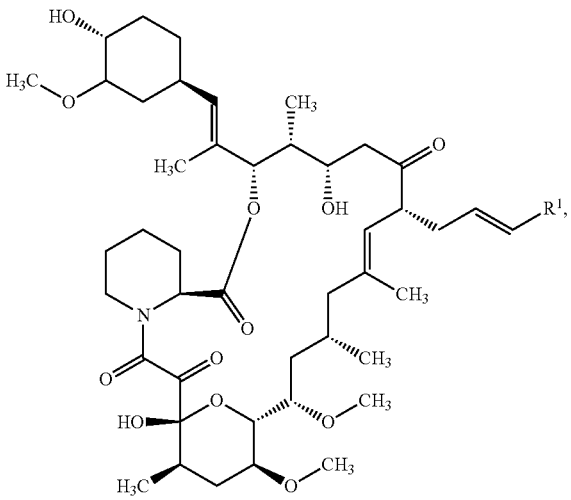

7. A pharmaceutical composition comprising a compound of claim 1 and a pharmaceutically acceptable carrier.

8. A method for treating a disease that causes fibrosis or diseases associated with tau aggregation, wherein the method comprises administering to a subject a therapeutically effective amount of a compound or a pharmaceutically acceptable salt of the compound with a chemical structure:

Formula I wherein R¹ is independently selected from a group consisting of:

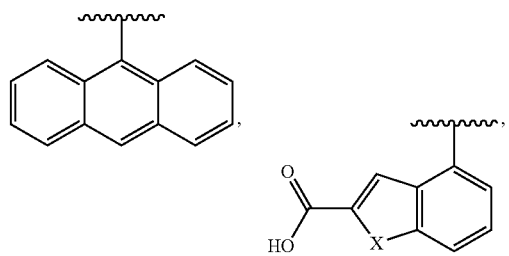

-continued

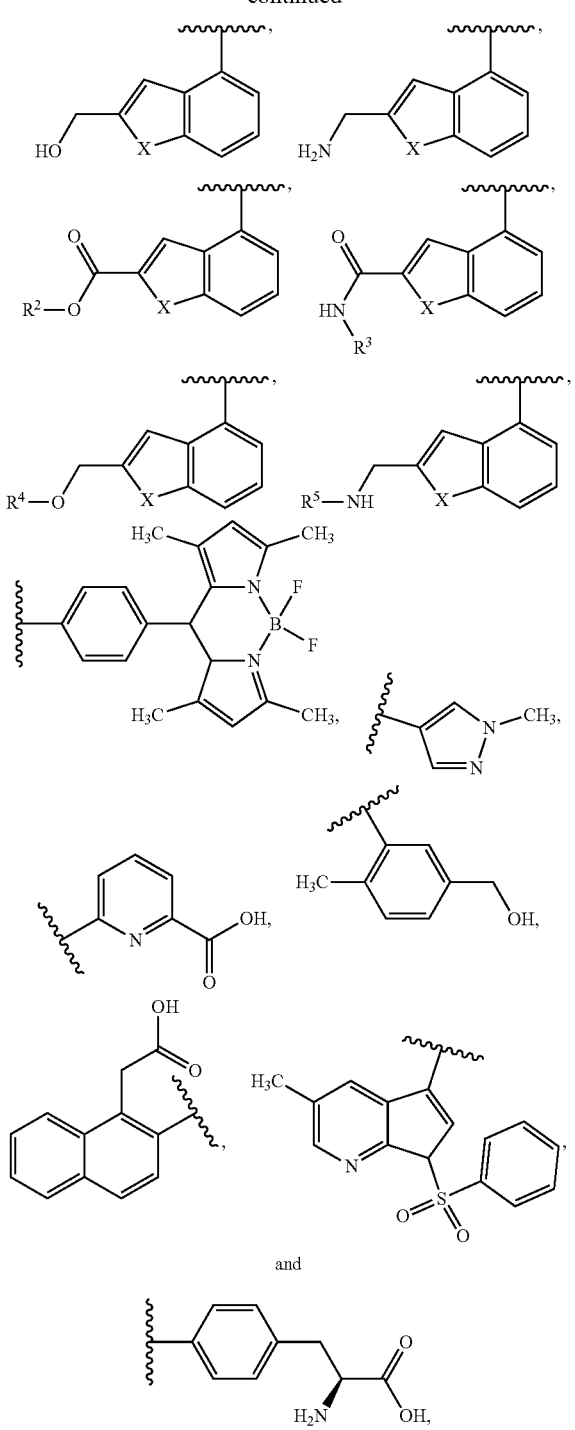

and wherein $R^2$, $R^3$, $R^4$, and $R^5$ are independently selected from a group consisting of: H, ketone, ether, acyl halide, carbonyl, aldehyde, carbonate ester, carboxyl, amide, amines, cyanate, isocynate, nitrate, nitrile, isonitrile, nitroso, oxime, borono, borinate, phosophino, phosphono, phosphate, thiol, sulfide, disulfide, sulfinyl, sulfino, sulfo, thiocyanate, isothiocyanate, carbonothioyl, $(C_{1-4})$alkyl, and $(C_{2-4})$alkenyl, and wherein X is independently selected from a group consisting of: $CH_2$, S, NH, and O.

9. The method of claim 8, wherein the compound comprises formula I $R^1$:

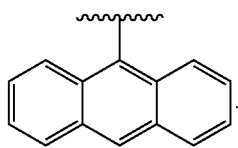 [SMILES: *c1c2ccccc2cc2ccccc12]

10. The method of claim 8, wherein the compound comprises formula I $R^1$ selected from a group consisting of:

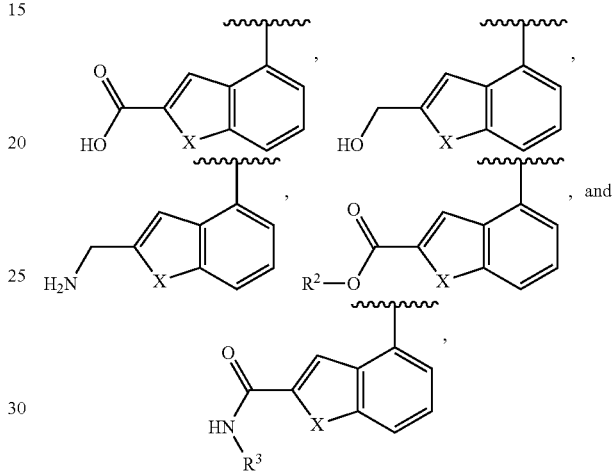

wherein $R^2$ and $R^3$ are independently selected from a group consisting of: H, ketone, ether, acyl halide, carbonyl, aldehyde, carbonate ester, carboxyl, amide, amines, cyanate, isocynate, nitrate, nitrile, isonitrile, nitroso, oxime, borono, borinate, phosophino, phosphono, phosphate, thiol, sulfide, disulfide, sulfinyl, sulfino, sulfo, thiocyanate, isothiocyanate, carbonothioyl, $(C_{1-4})$alkyl, and $(C_{2-4})$alkenyl, and wherein X is independently selected from a group consisting of: $CH_2$, S, NH, and O.

11. The method of claim 8, wherein the compound comprises formula I $R^1$ selected from a group consisting of:

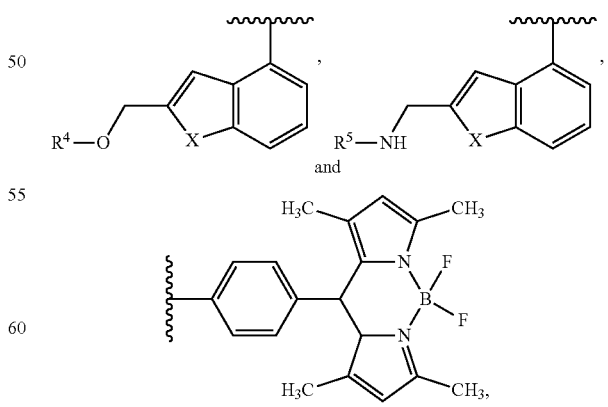

wherein $R^4$ and $R^5$ are independently selected from a group consisting of: H, ketone, ether, acyl halide, carbonyl, aldehyde, carbonate ester, carboxyl, amide, amines, cyanate, isocynate, nitrate, nitrile, isonitrile, nitroso, oxime, borono, borinate, phosophino, phosphono, phosphate, thiol, sulfide, disulfide, sulfinyl, sulfino, sulfo, thiocyanate, isothiocyanate, carbonothioyl, $(C_{1-4})$alkyl, and $(C_{2-4})$alkenyl, and wherein X is independently selected from a group consisting of: $CH_2$, S, NH, and O.

12. The method of claim 8, wherein the compound comprises formula I $R^1$ selected from a group consisting of:

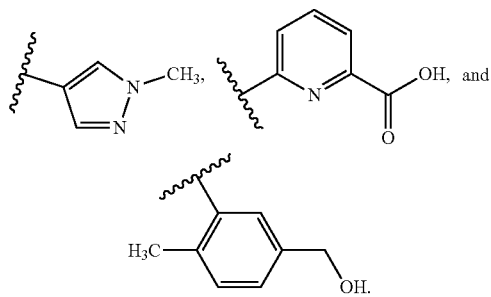

13. The method of claim 8, wherein the compound comprises formula I $R^1$ selected from a group consisting of:

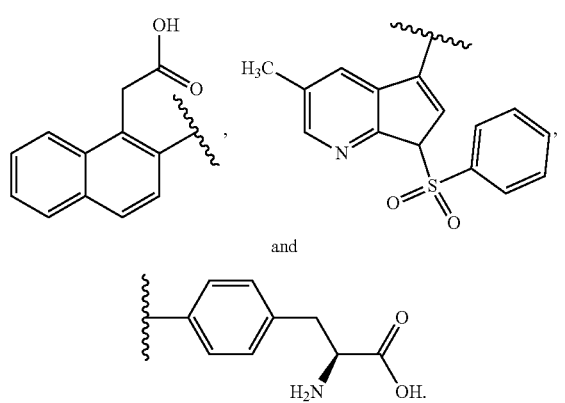

14. The method of claim 8, wherein the disease is selected from a list consisting of: idiopathic pulmonary fibrosis, amyotropic lateral sclerosis, Alzheimer's disease, Parkinson's disease, Huntington's disease, and tauopathy.

15. The method of claim 8, wherein the disease comprises idiopathic pulmonary fibrosis or Parkinson's disease.

16. The method of claim 8, wherein the compound comprises formula I $R^1$ selected from a group consisting of:

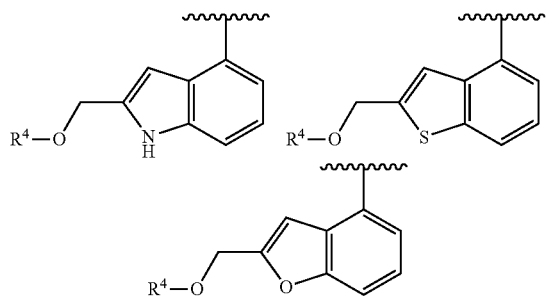

wherein $R^4$ is selected from a group consisting of: H, ketone, ether, carbonyl, carbonate ester, carboxyl, and phosphate.

17. The method of claim 8, wherein the compound comprises formula I $R^1$ selected from a group consisting of:

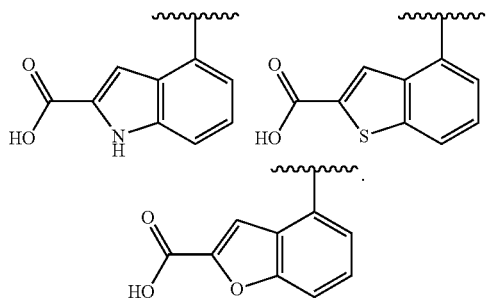

18. The method of claim 8, wherein the compound comprises formula I $R^1$ selected from a group consisting of:

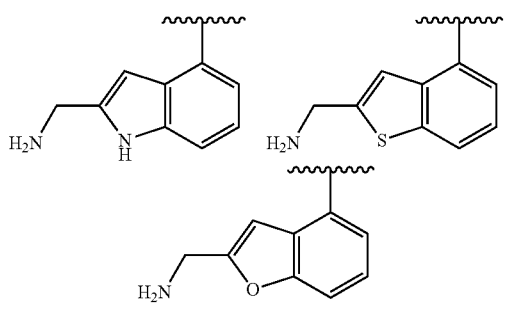

wherein $R^4$ is selected from a group consisting of: H, ketone, ether, carbonyl, carbonate ester, carboxyl, and phosphate.

19. The method of claim 8, wherein the compound comprises formula I $R^1$ selected from a group consisting of:

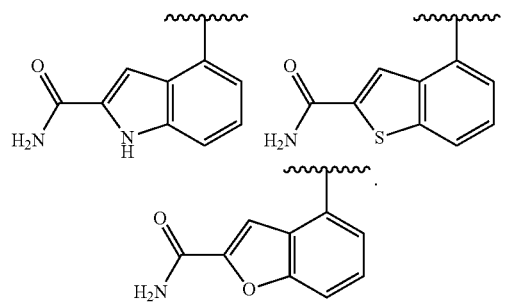

20. The method of claim 8, wherein the compound comprises formula I $R^1$ selected from a group consisting of:

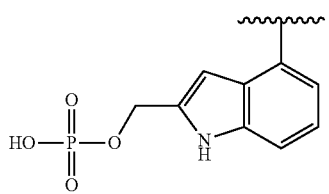

-continued
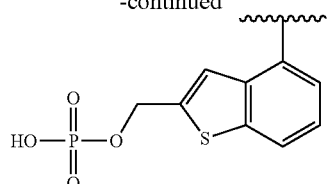
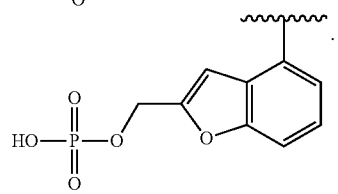
* * * * *